(12) United States Patent
Cho et al.

(10) Patent No.: US 8,530,200 B2
(45) Date of Patent: Sep. 10, 2013

(54) CORYNEBACTERIA STRAIN FOR ENHANCEMENT OF 5'-GUANOSINE MONOPHOSPHATE PRODUCTIVITY AND A METHOD OF PRODUCING 5'-GUANOSINE MONOPHOSPHATE USING THE SAME

(75) Inventors: Jinman Cho, Gyeonggi-do (KR); Hye Won Kim, Gyeonggi-do (KR); Yoon Seok Oh, Gyeonggi-do (KR); Jang Hee Park, Gyeonggi-do (KR)

(73) Assignee: CJ Cheiljedang Corporation, Seoul (KR)

( * ) Notice: Subject to any disclaimer, the term of this patent is extended or adjusted under 35 U.S.C. 154(b) by 39 days.

(21) Appl. No.: 13/140,302

(22) PCT Filed: Dec. 17, 2009

(86) PCT No.: PCT/KR2009/007558
§ 371 (c)(1),
(2), (4) Date: Jun. 16, 2011

(87) PCT Pub. No.: WO2010/071366
PCT Pub. Date: Jun. 24, 2010

(65) Prior Publication Data
US 2011/0250651 A1    Oct. 13, 2011

(30) Foreign Application Priority Data
Dec. 17, 2008 (KR) .................... 10-2008-0128846

(51) Int. Cl.
*C12P 19/32* (2006.01)
*C12P 19/30* (2006.01)

(52) U.S. Cl.
USPC ............................................ 435/92; 435/89

(58) Field of Classification Search
None
See application file for complete search history.

(56) References Cited

U.S. PATENT DOCUMENTS

| | | | | |
|---|---|---|---|---|
| 3,586,604 | A | * 6/1971 | Yamamoi | 435/89 |
| 3,922,193 | A | * 11/1975 | Enei et al. | 435/92 |
| 2002/0028490 | A1 | * 3/2002 | Molenaar et al. | 435/106 |
| 2007/0141682 | A1 | * 6/2007 | Park et al. | 435/117 |

FOREIGN PATENT DOCUMENTS

| | | |
|---|---|---|
| JP | 2007-512850 | 10/2000 |
| JP | 2000-270888 A | 5/2007 |
| KR | 10-2000-0076897 A | 12/2000 |
| KR | 10-2004-0014489 A | 2/2004 |
| KR | 10-2008-0025355 A | 3/2008 |
| WO | WO2006/059877 A1 | 6/2006 |
| WO | WO2008/033001 A1 | 3/2008 |

OTHER PUBLICATIONS

A. Maruyama et al., "ATP production from adenine by a self-coupling enzymatic process: High-level accumulation under ammonium-limited conditions", Biosci. Biotechnol. Biochem. 65 (3):644-650, 2001.
S. Mitsuhashi, et al., "Disruption of Malate:Quinone Oxidoreductase Increases L-Lysine Production by *Corynebacterium glutamicum*", Biosci. Biotechnol. Biochem. 70 (11):2803-2806, 2006.
M. E. Van Der Rest, et al., "Functions of the Membrane-Associated and Cytoplasmic Malate Dehycrogenase in the Citric Acid Cycle of *Escherichia coli*", Journal of Bacteriology 182 (24):6892-6899, 2000.
International Search Report and Written Opinion from PCT/KR2009/007558, dated Sep. 7, 2010.
Molenaar, et al.: Biochemical and genetic characterization of the membrane-associated malate dehydrogenase (acceptor) from *Corynebacterium glutamicum*; Eur. J. Biochem., 1998, vol. 254; pp. 395-403.

* cited by examiner

*Primary Examiner* — Blaine Lankford, Jr.
*Assistant Examiner* — Charles Zoltan Constantine
(74) *Attorney, Agent, or Firm* — Lathrop & Gage LLP; Brian C. Trinque; Michael Biro

(57) ABSTRACT

Disclosed is a method of producing 5'-guanosine monophosphate using a novel microorganism which has a malate dehydrogenase activity higher than that of a wild-type, thereby showing improved ATP productivity. Also, a novel microorganism is disclosed. The method comprises: culturing the *corynebacteria* strain which is enhanced in malate dehydrogenase activity over the endogenous activity, thus producing ATP in high yield; producing XMP in the culture; adding to the culture an enzyme or microorganism having XMP amination activity; and obtaining GMP from the culture.

3 Claims, 1 Drawing Sheet

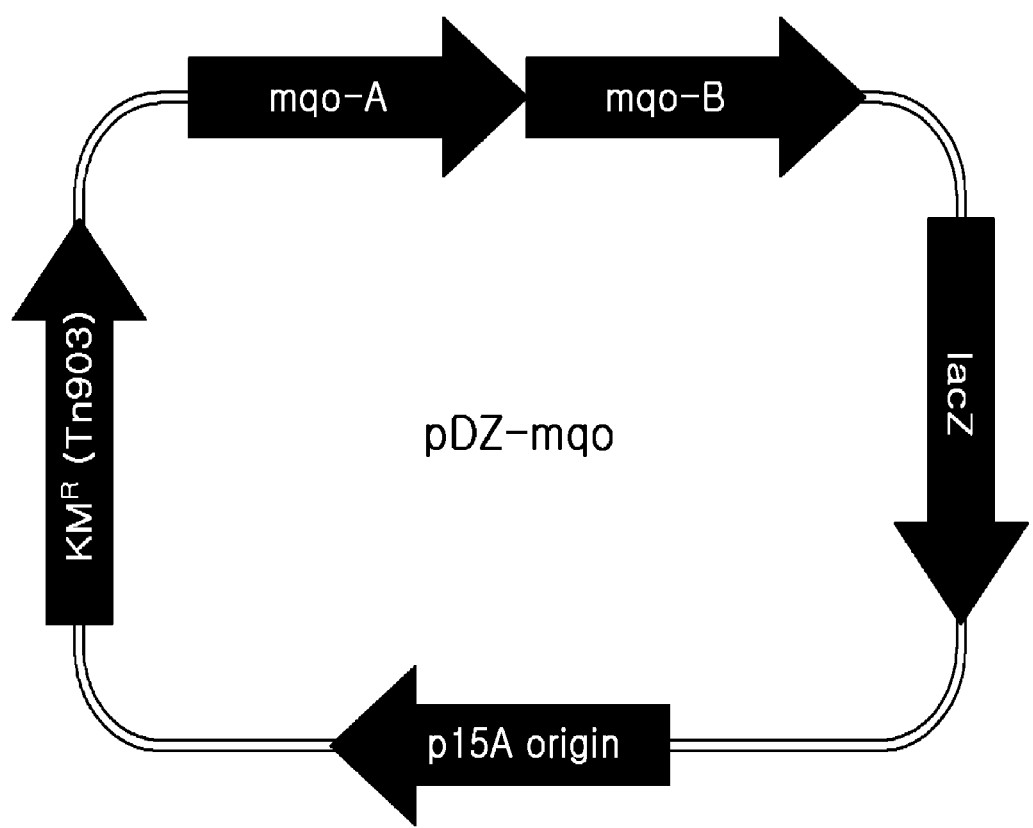

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: forward primer for mqo-A

<400> SEQUENCE: 1
gctctagaat cggtcattcc atgaaccc                                      28

<210> SEQ ID NO 2
<211> LENGTH: 29
<212> TYPE: DNA
<213> ORGANISM: Artificial Sequence
<220> FEATURE:
<223> OTHER INFORMATION: reverse primer for mqo-A

<400> SEQUENCE: 2
cgcggatccc atcgatatcg ccaactcca                                     29

<210> SEQ ID NO 3
<211> LENGTH: 29
<212> TYPE: DNA
<213> ORGANISM: Artificial Sequence
<220> FEATURE:
<223> OTHER INFORMATION: forward primer for mqo-B

<400> SEQUENCE: 3
cgcggatcca tcggtcattc catgaaccc                                     29

<210> SEQ ID NO 4
<211> LENGTH: 28
<212> TYPE: DNA
<213> ORGANISM: Artificial Sequence
<220> FEATURE:
<223> OTHER INFORMATION: reverse primer for mqo-B

<400> SEQUENCE: 4
gctctagaca tcgatatcgc caactcca                                      28

<210> SEQ ID NO 5
<211> LENGTH: 18
<212> TYPE: DNA
```

<213> ORGANISM: Artificial Sequence
<220> FEATURE:
<223> OTHER INFORMATION: forward primer for detecting mqo

<400> SEQUENCE: 5
cttttcgatg acgcccaa                                                    18

<210> SEQ ID NO 6
<211> LENGTH: 21
<212> TYPE: DNA
<213> ORGANISM: Artificial Sequence
<220> FEATURE:
<223> OTHER INFORMATION: reverse primer for detecting mqo

<400> SEQUENCE: 6
ccactttatc gggtgagacc a                                                21

<210> SEQ ID NO 7
<211> LENGTH: 1503
<212> TYPE: DNA
<213> ORGANISM: Corynebacterium ammoniagenes

<400> SEQUENCE: 7

| | | | | | |
|---|---|---|---|---|---|
| atgtcagatt | ccccgaagaa | cgcaccgagg | attaccgatg | aggcagatgt | agttctcatt | 60 |
| ggtgccggta | tcatgagctc | cacgctgggt | gcaatgctgc | gtcagctgga | gccaagctgg | 120 |
| actcagatcg | tcttcgagcg | tttggatgga | ccggcacaag | agtcgtcctc | cccgtggaac | 180 |
| aatgcaggaa | ccggccactc | tgctctatgc | gagctgaact | acaccccaga | ggttaagggc | 240 |
| aaggttgaaa | ttgccaaggc | tgtaggaatc | aacgagaagt | tccaggtttc | ccgtcagttc | 300 |
| tggtctcacc | tcgttgaaga | gggagtgctg | tctgatccta | aggaattcat | caaccctgtt | 360 |
| cctcacgtat | ctttcggcca | gggcgcagat | caggttgcat | acatcaaggc | tcgctacgaa | 420 |
| gctttgaagg | atcacccact | cttccagggc | atgacctacg | ctgacgatga | agctaccttc | 480 |
| accgagaagc | tgcctttgat | ggcaaagggc | cgtgacttct | ctgatccagt | agcaatctct | 540 |
| tggatcgatg | aaggcaccga | catcaactac | ggtgctcaga | ccaagcagta | cctggatgca | 600 |
| gctgaagttg | aaggcactga | aatccgctat | ggccacgaag | tcaagagcat | caaggctgat | 660 |
| ggcgcaaagt | ggatcgtgac | cgtcaagaac | gtacacactg | cgacaccaa | gaccatcaag | 720 |
| gcaaacttcg | tgttcgtcgg | cgcaggcgga | tacgcactgg | atctgcttcg | cagcgcaggc | 780 |
| atcccacagg | tcaagggctt | cgctggattc | ccagtatccg | gcctgtggct | tcgttgcacc | 840 |
| aacgaggaac | tgatcgagca | gcacgcagcc | aaggtatatg | caaggcatc | tgttggcgct | 900 |
| cctccaatgt | ctgttcctca | ccttgacacc | cgcgttatcg | agggtgaaaa | gggtctgctc | 960 |
| tttggaccctt | acggtggctg | gaccccctaag | ttcttgaagg | aaggctccta | cctgacctg | 1020 |
| ttcaagtcca | tccgcccaga | caacattcct | tcctaccttg | gcgttgctgc | tcaggaattt | 1080 |
| gatctgacca | agtaccttgt | cactgaagtt | ctcaaggacc | aggacaagcg | tatggatgct | 1140 |
| cttcgcgagt | acatgccaga | ggcacaaaac | ggcgattggg | agaccatcgt | tgccggacag | 1200 |
| cgtgttcagg | ttattaagcc | tgcaggattc | cctaagttcg | gttccctgga | attcggcacc | 1260 |
| accttgatca | caactccga | aggcaccatc | gccggattgc | tcggtgcttc | ccctggagca | 1320 |
| tccatcgcac | cttccgcaat | gatcgagctg | cttgagcgtt | gcttcggtga | ccgcatgatc | 1380 |
| gagtggggcg | acaagctgaa | ggacatgatc | ccttcctacg | gcaagaagct | tgcttccgag | 1440 |
| ccagcactgt | ttgagcagca | gtgggcacgc | acccagaaga | ccctgaagct | tgaggaagcc | 1500 |
| taa | | | | | | 1503 |

CORYNEBACTERIA STRAIN FOR ENHANCEMENT OF 5'-GUANOSINE MONOPHOSPHATE PRODUCTIVITY AND A METHOD OF PRODUCING 5'-GUANOSINE MONOPHOSPHATE USING THE SAME

The present application claims the benefit of priority of International Application No. PCT/KR2009/007558, filed Dec. 17, 2009, which claims priority to Korean Patent Application No. 10-2008-0128846, filed Dec. 17, 2008. The entire contents of each of the above documents are incorporated herein by reference.

TECHNICAL FIELD

The present invention relates to a *Corynebacteria* strain having higher than the endogenous malate dehydrogenase activity which can therefore produce ATP in higher yield. Also, the present invention is concerned with a method of producing 5'-guanosine monophosphate using the *Corynebacteria* strain in combination with an enzyme or a microorganism having amination activity.

BACKGROUND ART

5'-Guanosine monophosphate (hereinafter referred to as "GMP") is a food additive widely used as a flavor enhancer, like inosine monophosphate (hereinafter referred to as "IMP"). GMP elicits an umami taste and its use is dependent on monosodium glutamate (MSG) also being used. It is often used in synergy with IMP to increase the intensity of the umami taste of MSG.

Examples of the methods for the preparation of GMP known thus far include (1) the enzymatic degradation of yeast RNA, (2) direct microorganism fermentation to GMP, (3) microorganism fermentation to guanosine, followed by chemical phosphorylation, (4) microorganism fermentation to guanosine, followed by enzymatic phosphorylation, (5) microorganism fermentation to xanthosine 5'-monophosphate (hereinafter referred to as "XMP"), followed by conversion into GMP by a *corynebacteria* strain, and (6) microorganism fermentation to XMP, followed by conversion of XMP into GMP by *Escherichia coli* which has aminase activity. Of them, method (1) has difficulties of material supply and is economically non-beneficial and method (2) suffers from the disadvantage of being of low yield due to the membrane permeability of GMP. Thus, the other methods are widely used in industrial applications.

For method (6) in which XMP is produced and converted into GMP, it is critical to provide ATP as a cofactor. Most of the ATP used in the conversion of XMP to GMP is supplied from an XMP-producing strain. In the conversion approach, xylene plays an important role because it increases the membrane permeability of ATP and XMP. Xylene in the medium allows ATP and XMP to penetrate into a GMP-producing strain, followed by the conversion of XMP into GMP. Therefore, the approach to GMP production takes the strategy of increasing ATP productivity.

The conversion from XMP into GMP is represented by the following reaction formula:

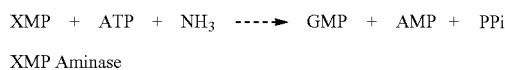

That is, a continuous supply of ATP, serving as a cofactor, is essential for the GMP-producing process in which XMP is primarily produced by an XMP-producing strain and then converted into GMP in the presence of an enzyme or microorganism having XMP aminase activity. Thus, it is very important to enhance ATP productivity of the XMP-producing strain. The AMP produced in the conversion process is reused as a substrate for ATP production. In fact, adenine-based nucleotides are recycled for the production of ATP.

Hence, increased ATP productivity of the XMP-producing strain is necessary for GMP production in high yield. The activity of malate dehydrogenase has a great influence on the production of ATP. However, nowhere are microorganisms and methods which are designed to enhance malate dehydrogenase activity for increasing GMP production yields mentioned in previous documents.

Keeping in the mind that it is important to increase the ATP productivity of the XMP-producing strain in order to increase GMP yield with priority over the two-step conversion, the present inventors conducted intensive research and found a gene which is responsible for the increase. Also, it was found that when used in combination with XMP animase, a *Corynebacteria* strain transformed with a recombinant vector carrying two copies of the gene in tandem, could produce XMP and ATP in high yields, thus increasing GMP productivity.

DISCLOSURE OF INVENTION

Technical Problem

It is therefore an object of the present invention to provide a *Corynebacteria* strain having higher than the endogenous malate dehydrogenase activity which can therefore produce ATP in higher yield.

It is another object of the present invention to provide a method of producing GMP, comprising: culturing the transformed microorganism; producing XMP in the culture; adding to the culture an enzyme or microorganism having XMP amination activity; and obtaining GMP from the culture.

Solution to Problem

In accordance with an aspect thereof, the present invention is directed to a *corynebacteria* strain with enhancements over endogenous malate dehydrogenase activity, thus producing ATP in high yield. The *corynebacteria* strain of the present invention is modified to have malate dehydrogenase activity higher than endogenous activity, resulting in an enhancement in ATP productivity.

The term "malate dehydrogenase", as used herein, means an enzyme that catalyzes the conversion of malate into oxaloacetate by dehydrogenation. This enzyme is found in a very broad spectrum of living organisms with the accompaniment of lactate dehydrogenase and requires DPN and NAD as cofactors for its activity, these usually accompanying lactate dehydrogenase. In the *corynebacteria* strain according to the present invention, the malate dehydrogenase activity is increased to produce ATP in higher yield, resulting in an enhancement in GMP productivity.

As used herein, the term "endogenous activity" is intended to refer to the enzyme activity of interest in a wild-type microorganism. The term "higher than endogenous activity" means increased enzyme activity compared to the activity of the endogenous variety, whether resulting from an activity increase by the enzyme itself or by an endogenous gene or a foreign gene. For example, an increase in enzyme activity may be achieved by any method well known in the art, including, but not limited to, increasing or decreasing the number of gene copies, replacing, modifying or mutating a promoter of interest, etc.

The target enzyme malate dehydrogenase whose activity is sought to be increased according to the present invention is encoded by the mqo gene of *Corynebacteria*. As long as it is biologically identical or correspondends to the mqo gene, any derivative or analog may be used in the present invention. That is, if its activity is substantially the same as or similar to that of the mqo gene, any gene falling within the range of the mqo gene is useful in the present invention. Advantageously, the gene useful in the present invention shares at least 70%, more preferably at least 80%, even more preferably at least 90%, even far more preferably at least 95% and most preferably at least 98% homology with the sequence of the mqo gene. More advantageously, the malate dehydrogenase is encoded by the nucleotide sequence of SEQ ID NO.: 7. The increase of gene copies can be achieved by the introduction of exogenous genes and/or the amplification of endogenous genes. The number of gene copies may be readily determined by those skilled in the art according to need and purpose. The amplification of the endogenous gene can also be conducted using a method known in the art, for example, by culturing in a suitable selective medium under pressure. In a preferred example, a vector carrying a gene coding for malate dehydrogenase is introduced into a *corynebacteria* strain to generate a transformed microorganism with an enhancement over the endogenous activity.

As long as it is known in the art and belongs to the *corynebacteria* genus, any strain may be used in the present invention without limitation. Preferably, examples of the *corynebacteria* strain useful in the present invention include *Corynebacterium ammoniagenes*, *Corynebacterium glutamicum*, *Brevibacterium flavum*, and *Brevibacterium lactofermentum*, but are not limited thereto. In detail, among the *corynebacteria* strains are *Corynebacterium ammoniagenes* ATCC6872, *Corynebacterium thermoaminogenes* FERM BP-1539, *Corynebacterium glutamicum* ATCC 13032, *Corynebacterium glutamicum* R, *Brevibacterium flavum* ATCC 14067, *Brevibacterium lactofermentum* ATCC 13869 and derivatives thereof. Preferred is *Corynebacterium ammoniagenes* KCJ-1304 transformed from *Corynebacterium ammoniagenes* KCCM-10530.

A recombinant vector carrying an mqo gene may be used to generate a microorganism capable of producing ATP in high yield.

As used herein, the term "mqo gene", an abbreviation of "malate:quinone oxidoreductase" gene, means a gene coding for malate oxaloacetate which functions to oxidize malate to oxaloacetate.

As long as it carries an mqo gene, any usual recombinant vector can be employed in the present invention without limitation. Preferable is pDZ-mqo. In a preferred example of the present invention, the mqo gene containing SEQ ID NO. 7 was employed to construct a recombinant pDZ-mqo vector (see FIG. 1).

The term "vector", as used herein, means a DNA molecule used as a vehicle to transfer foreign genetic material into a suitable host cell and is a DNA construct containing regulatory elements which allow a transgene to do recombination with a host genome. Preferably, the recombinant vector carrying the mqo vector in accordance the present invention may have the structure shown in the cleavage map of FIG. 1. The vector represented by the cleavage map of FIG. 1 may be introduced into *corynebacteria* sequentially or simultaneously. In accordance with a preferred embodiment of the present invention, the recombinant vector is transformed into *Corynebacterium ammoniagenes* KCCM-10530 which is then cultured in a selective medium to allow two copies of the mqo gene to incorporate into the genome of the host through homologous recombination, resulting in the generation of a *Corynebacterium ammoniagenes* mutant, named *Corynebacterium ammoniagenes* KCJ-1304. It was deposited with accession number KCCM10972P.

In accordance with another aspect thereof, the present invention is directed into a *corynebacteria* strain transformed with a recombinant vector carrying an mqo gene. The *corynebacteria*-derived mqo gene may be used using a transformation method known in the art without limitation. Preferably, the mqo gene is cloned in a vector for use in transformation into cells.

Any method may be employed for transformation if it is known in the art. As used herein, the term "transformation" is the genetic alteration of a cell resulting from the uptake, genomic incorporation and expression of foreign DNA. Typical transformation methods include $CaCl_2$ precipitation, a Hanahan method in which the effect of $CaCl_2$ precipitation is improved in combination with DMSO (dimethyl sulfoxide), electroporation, calcium phosphate transfection, protoplast fusion, silicon carbide fiber-mediated transformation, *agrobacterium*-mediated transformation, PEG-mediated transformation, dextran sulfate, lipofectamine, and desiccation/inhibition-mediated transformation. Transformation with pDZ-mqo in accordance with the present invention is not limited to the examples of transformation, but can be achieved using any method known in the art without limitation.

*Corynebacterium ammoniagenes* KCCM10972P has two copies of mqo gene incorporated into the genome thereof resulting from the introduction thereinto of pDZ-mqo having the structure shown in the cleavage map of FIG. 1 and the homologous recombination of two copies of mqo gene with the endogenous gene.

In accordance with a further aspect thereof, the present invention is directed to a method of producing GMP, comprising: (a) culturing the *corynebacteria* strain which is enhanced in malate dehydrogenase activity over the endogenous activity, thus producing ATP in high yield; (b) producing XMP in the culture; (c) adding to the culture an enzyme or microorganism having XMP amination activity; and (d) obtaining GMP from the culture. In the present invention, XMP is produced in higher yield from the transformed microorganism and then converted into GMP in the presence of XMP aminase or a microorganism having XMP amination activity. Preferably, the transformed microorganism is the *corynebacteria* strain which is enhanced in malate dehydrogenase activity over the endogenous activity.

Any medium known in the art may be used without limitation in culturing the strain capable of producing XMP or GMP. Preferably, the medium contains glucose as a carbon source and optionally various other carbon sources. For use in culturing a microorganism of interest, a medium must meet requirements for the growth of the microorganism. Culture media for *corynebacteria* strains are known in the art (e.g., Manual of Methods for General Bacteriology. American Society for Bacteriology. Washington D.C., USA, 1981). Examples of the carbon sources useful for *corynebacteria* strains include sugars and carbohydrates such as glucose, saccharose, lactose, fructose, maltose, starch, cellulose, etc., oils and lipids such as soybean oil, sunflower oil, castor oil, coconut oil, etc., fatty acids such as palmitic acid, stearic acid, linolenic acid, etc., alcohols such as glycerol, ethanol, etc., and organic acids such as acetic acid. These carbon sources may be used individually or in combination. Organic materials such as peptone, yeast extract, beef extract, malt extract, corn steep liquor, soybean, etc., urea, and inorganic compounds such as ammonium chloride, ammonium phosphate, ammonium carbonate and ammonium nitrate may be used individually or in combination as nitrogen sources in the medium. Potassium dihydrogen phosphate or dipotassium hydrogen phosphate, or corresponding sodium salts may be useful as phosphorus sources. In addition, the culture medium may contain metal salts such as magnesium sulfate, iron sulfate, etc. Further, amino acids and/or vitamins may be required as essential elements. The culture medium may also contain suitable precursors. These materials may be added to a medium in a batch manner or continuous manner.

The culture medium may be adjusted in pH by basic compounds such as sodium hydroxide, potassium hydroxide, ammonia, etc. or acid compounds such as phosphoric acid or sulfuric acid. An antifoaming agent such as fatty acid polyglycol ester may be used to prevent the generation of bubbles during the culturing. The medium may be aerated with oxygen or oxygen-containing gas (e.g., air) to maintain an aerobic condition or with nitrogen, hydrogen or carbon dioxide gas to maintain an anaerobic condition. Culturing temperature is usually maintained at 20° C.~45° C., and preferably at 30° C.~35° C. Culturing is continued until the maximum amount of XMP or GMP is obtained. In this regard, a time period of from 10 to 160 hours is required.

The microorganism having XMP amination activity useful in the present invention may be *Escherichia coli*. *E. coli* having XMP amination activity may be cultured using any of the methods well known in the art. The culture medium for the *E. coli* may contain various nutrients including inorganic nitrogen sources such as ammonia, ammonium chloride, ammonium sulfate, etc., organic nitrogen sources such as peptone, NZ-amine, beef extract, yeast extract, corn steep liquor, casein hydrolysate, fish or fish meal, defatted soybean cake or meal, and inorganic compounds such as potassium monohydrogen phosphate, potassium dihydrogen phosphate, magnesium sulfate, ferrous sulfate, manganese sulfate, and calcium carbonate. When needed, vitamins and auxotrophic bases may be used. For the culture, shaking culture or stirring culture by aeration may be used. Temperature of the culture ranges from 30 to 45° C., and preferably from 37 to 40° C. During culturing, it is preferable that the pH be adjusted to a fairly neutral level. The culturing period is 1 to 2 days. As a result, the microorganism having XMP amination activity accumulates in the culture medium.

In the present invention, a culture medium containing XMP is added to the culture of *E. coli* having XMP amination activity to convert XMP into GMP. In this regard, the conversion of XMP into GMP may be achieved with a compound which increases the membrane permeability of XMP, such as xylene. Xylene facilitates the entrance of XMP from the culture medium into the GMP-producing strain. Compounds useful for increasing the membrane permeability of XMP are well known in the art. Examples of such compounds include a hydrophobic material (e.g., xylene, toluene, benzene, ethyl acetate), a surfactant (cationic surfactants, e.g., polyoxyethylenestearylamine, cetyltrimethylammonium bromide, Cation FB and Cation F2-40E; anionic surfactants, e.g., sodium oleylamide sulfate, Newrex TAB, and Rapizole 80), and a metal ion (e.g., calcium ion, magnesium ion), but are not limited thereto. The amount of the compound for increasing the cell membrane permeability of XMP varies depending on the characteristics thereof, and can be appropriately adjusted by those of ordinary skill in the art.

The GMP thus produced may be secreted into the culture medium or remain within the cell. The method of producing GMP in accordance with the present invention comprises recovering GMP from the cells or the culture medium. For the recovery of GMP from cells or culture media, any method well known in the art may be utilized. Examples of such methods include filtration, anionic exchange chromatography, crystallization, and HPLC, but are not limited thereto.

As used herein, the term "guanosine monophosphate" is a nucleotide, composed of guanosine and phosphate, found in RNA. The phosphate moiety may be positioned at 5', 3' or 2', which are named 5'-, 3'- or 2'-form, respectively. In the present invention, GMP(5'-guanosine monophosphate) is produced as a colorless needle-shaped crystal, and exists in free form within the body. It has a molecular formula of $C_{10}H_{14}N_5O_8P$. Guanosine monophosphate in the form of its salts, such as disodium guanylate, dipotassium guanylate and calcium guanylate, are food additives used as nucleic acid-based flavor enhancers to provide the taste of mushroom. When using the transformed microorganism in accordance with the present invention, GMP can be produced in a high yield which is found to be improved by about 8.5% compared to conventional microorganisms.

Advantageous Effects of Invention

Transformed with the recombinant vector in accordance with the present invention, the *corynebacteria* strain shows improved malate dehydrogenase activity and thus produces ATP in increased yield. When applied to the conversion of GMP from XMP, the transformed strain of the present invention allows higher productivity of GMP than do conventional microorganisms.

BRIEF DESCRIPTION OF DRAWINGS

FIG. 1 is a schematic diagram showing the structure of the recombinant vector pDZ-mqo in which two copies of an mqo gene are inserted into a pDZ vector.

MODE FOR THE INVENTION

A better understanding of the present invention may be obtained through the following examples which are set forth to illustrate, but are not to be construed as limiting the present invention.

EXAMPLE 1

Cloning of the XMP-Producing Strain
*Corynebacterium ammoniagenes*
KCCM-10530-Derived mqo and Construction of
Recombinant Vector (pDZ-mqo) for Genomic
Incorporation The nucleotide sequence of the mqo gene (NCBI ID_3345228) was obtained from data from the NIH GenBank. Based on the sequence, two pairs of primers (SEQ ID NOs. 1 to 4) were synthesized.

While the genome of *Corynebacterium* KCCM-10530 served as a template, PCR was conducted in the presence of the high-fidelity DNA polymerase PfuUltra™ (Stratagene) using the primers of SEQ ID NOs. 1 to 4, with 25 cycles of denaturing at 95° C. for 30 sec, annealing at 55° C. for 30 sec and extension at 68° C. for 2 min. The PCR products thus obtained were two copies of the mqo gene, each 2.1 kb long (mqo-A, mqo-B), which were amplified using two sets of SEQ ID NOs: 1 and 2, and SEQ ID NOs: 3 and 4, respectively.

```
SEQ ID NO: 1    gctctagaATCGGTCATTCCATGAACCC;

SEQ ID NO: 2    cgcggatccCATCGATATCGCCAACTCCA;

SEQ ID NO: 3    cgcggatccATCGGTCATTCCATGAACCC;

SEQ ID NO: 4    gctctagaCATCGATATCGCCAACTCCA;
```

After being treated with suitable restriction enzymes (mqo-A: XbaI+BamHI, mqo-B: BamHI+XbaI), the PCR products mqo-A and mqo-B were inserted into the pDZ vector which was previously treated with XbaI and shrimp alkaline phosphotase, through the three-piece junction (see Korean Patent Application No. 10-2007-94433). Finally, a recombinant pDZ-mqo vector in which two copies of the mqo gene were cloned in tandem was obtained. FIG. 1 is a schematic diagram showing the structure of the recombinant pDZ-mqo vector for incorporation into *Corynebacterium* genome.

EXAMPLE 2

Generation of an mqo-Inserted Strain

The pDZ-mqo vector construct was transformed into the KCCM-10530 strain and subjected to homologous recombination with the genome to insert one mqo gene copy at a position adjacent to the mqo gene on the genome. Thus, a novel XMP-producing strain, named *Corynebacterium ammoniagenes* KCJ-1304, which had two copies of the mqo gene on the genome thereof, was obtained. The insertion of two copies of the mqo gene in tandem was identified using PCR using a set of primers (SEQ ID NOs. 5 and 6) which targeted nucleotide sequences upstream and downstream of the two copies of the mqo gene.

```
SEQ ID NO. 5:    CTTTTCGATGACGCCCAA

SEQ ID NO. 6:    CCACTTTATCGGGTGAGACCA
```

EXAMPLE 3

Malate Dehydrogenase Activity of the mqo-Inserted Strain

The XMP-producing *Corynebacterium ammoniagenes* KCJ-1304 prepared in Example 2 was assayed for malate dehydrogenase activity as follows. The strain was inoculated into a medium containing 10 g/l bactopeptone, 5 g/l bacto-beef extract, 5 g/l bacto-yeast extract, 2.5 g/l NaCl, 50 mg/l adenine, and 50 mg/l guanine and incubated at 30° C. for 12 hrs until OD 10 was obtained. 10 mL of the cell culture was recovered, washed twice with buffer comprising 50 mM HEPES, 10 mM potassium acetate, 10 mM $CaCl_2$ and 10 mM $MgCl_2$, and suspended in 1 mL of the same buffer. After interruption using a sonicator, the cell lysate was centrifuged. The supernatant was recentrifuged to give a pellet which was then suspended in 100 μL of buffer. 10 μL of this suspension was used as an enzyme solution. A reaction buffer was prepared by mixing 50 mM HEPES, 10 mM potassium acetate and 50 μM 2,6-dichloroindolphenol ($Cl_2$Ind). $Cl_2$Ind was thawed and mixed just before reaction. To 980 μL of the reaction mixture were added 10 μL of 100 mM malate as a substrate and 10 μL of the enzyme solution, followed by incubation at 30° C. for 15 min with shaking. The enzyme activity was determined by measuring the concentration of reduced $Cl_2$Ind. $Cl_2$Ind had an absorption coefficient of 22 $cm^{-1}mM^{-1}$ at 600 nm.

TABLE 1

| Strain | KCCM-10530 | KCJ-1304 |
|---|---|---|
| Reduced $Cl_2$Ind (μM) | 15.45 | 20.17 |

As shown in Table 1, KCJ-1304 was observed to increase in malate dehydrogenase activity by 30.6% compared to the mother strain KCCM-10530.

EXAMPLE 4

ATP Level in the mqo-Inserted Strain

The XMP-producing strain *Corynebacterium ammoniagenes* KCJ-1304 prepared in Example 2 was measured for intracellular ATP level as follows.

The mother strain *Corynebacterium ammoniagenes* KCCM-10530 and the mutant KCJ-1304 were inoculated into respective 14 mL tubes, each containing 3 mL of the following seed medium, and incubated at 30° C. for 20 hrs with shaking at 200 rpm. Then, the seed cultures were added in an amount of 0.4 mL to 25 mL of the seed medium in respective 250 mL corner-baffle flasks, followed by shake-culture at 30° C. and 230 rpm for 20 hrs. The cell cultures were measured for OD and intracellular ATP levels. The mutant KCJ-1304 was found to produce ATP at a higher rate per OD than did the mother strain KCCM-10530, indicating that the mutant strain of the present invention might show higher GMP productivity compared to the mother strain. The results are summarized in Table 2, below.

TABLE 2

| Strain | OD(A562) | ATP Level(μM) | ATP Level/OD |
|---|---|---|---|
| KCCM-10530 | 20.76 | 32.92 | 1.59 |
| KCJ-1304 | 21.44 | 69.74 | 3.25 |

As shown in Table 2, the intracellular ATP level per OD of KCJ-1304 was increased by about 104% compared to that of the mother strain KCCM-10530.

EXAMPLE 5

XMP Fermentation and GMP Production of the mqo-Inserted Strain

The XMP-producing strain *Corynebacterium ammoniagenes* KCJ-1304 prepared in Example 2 was cultured to produce GMP as follows.

The mother strain *Corynebacterium ammoniagenes* KCCM-10530 and the mutant KCJ-1304 were inoculated into respective 14 mL tubes, each containing 3 mL of the following seed medium, and incubated at 30° C. for 20 hrs with shaking at 200 rpm. Then, the seed cultures were added in an amount of 0.4 mL to 32 mL of the following production medium (24 mL of main medium+8 mL of medium A) in respective 250 mL corner-baffle flasks, followed by shake culturing at 30° C. and 230 rpm for 96 hrs. In order to subject the XMP thus produced to GMP conversion, the following conversion additives and *E. coli* XMP aminase were added to the Erlenmeyer flasks, after which a conversion reaction was conducted at 40° C. for 4 hrs. The mutant KCJ-1304 was found to increase in conversion rate, which accounts for GMP production per consumed XMP, compared to the mother strain KCCM-10530. That is, the mutant strain of the present invention is improved in GMP productivity compared to the conventional strain. The results are summarized in Table 3, below.

TABLE 3

| Strain | Level (g/l) | | Conversion Rate (%) GMP produce/ XMP consumed |
|---|---|---|---|
| | XMP | GMP | |
| KCCM-10530 | 28.6 | 21.2 | 74.1 |
| KCJ-1304 | 30.3 | 23.0 | 75.9 |

As is apparent from the data of Table 3, KCJ-1304 was found to increase in conversion rate by 2.4% and in GMP level by 8.5% compared to the mother strain KCCM-10530.

Seed Medium: glucose 30 g/l, peptone 15 g/l, yeast extract 15 g/l, NaCl 2.5 g/l, urea 3 g/l, adenine 150 mg/l, guanine 150 mg/l, pH 7.2

Production Medium (main): glucose 80 g/l, magnesium sulfate 10 g/l, ferrous sulfate 20 mg/l, zinc sulfate 10 mg/l, manganese sulfate 10 mg/l, adenine 30 mg/l, guanine 30 mg/l, biotin 100 μg/l, copper sulfate 1 mg/l, thiamine chloride 5 mg/l, calcium chloride 10 mg/l, pH 7.2

Production Medium (medium A): monopotassium phosphate 10 g/l, dipotassium phosphate 10 g/l, urea 7 g/l, ammonium sulfate 5 g/l Conversion Additive: phytic acid 1.8 g/l, $MgSO_4$ 4.8 g/l, nymeen 3 ml/l, xylene 2%, adenine 100 mg/l, $Na_2HPO_4$ 7.7 g/l, glucose 46 g/l.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of producing 5'-guanosine monophosphate (GMP) comprising:
   (a) culturing a *Corynebacteria* mutant strain to prepare a culture solution containing adenosine triphosphate (ATP) and xanthosine 5'-monophosphate (XMP), wherein the mutant strain has improved ATP productivity, and wherein the mutant strain has a malate dehydrogenase activity higher than that of a wild-type *Corynebacteria* strain resulting from an increase in malate:quinone oxidoreductase (mqo) expression;
   (b) mixing the culture solution with an enzyme or a microorganism having XMP amination activity and culturing the resulting mixture, to thereby convert XMP into GMP; and
   (c) obtaining GMP from the mixture.

2. The method according to claim 1, wherein the *Corynebacteria* mutant strain has two copies of the malate:quinone oxidoreductase (mqo) gene incorporated into the genome.

3. The method according to claim 2, wherein the *Corynebacteria* mutant strain is *Corynebacterium ammoniagenes*.

* * * * *